United States Patent [19]

Eilertsen et al.

[11] Patent Number: 4,497,897
[45] Date of Patent: Feb. 5, 1985

[54] LIQUID PROTEINASE CONCENTRATE AND METHOD FOR PREPARATION

[75] Inventors: Jens H. Eilertsen, Virum; Arne D. Fog, Ballerup; Keith Gibson, Hvidovre, all of Denmark

[73] Assignee: Novo Industri A/S, Denmark

[21] Appl. No.: 448,374

[22] Filed: Dec. 9, 1982

[51] Int. Cl.$^3$ .......................... C12N 9/96; C11D 7/42
[52] U.S. Cl. ................................ 435/188; 252/174.12
[58] Field of Search ................. 252/174.12, DIG. 12; 435/188, 219, 220, 221, 222, 264

[56] References Cited

U.S. PATENT DOCUMENTS

| | | | |
|---|---|---|---|
| 3,717,550 | 2/1973 | Ziffer | 435/188 |
| 4,111,855 | 9/1978 | Barrat et al. | 252/545 |
| 4,305,837 | 12/1981 | Kaminsky et al. | 252/174.12 |
| 4,318,818 | 3/1982 | Letton et al. | 252/174.12 |

OTHER PUBLICATIONS

Aunstrup, K., Proteinases in Economic Microbiology, vol. 5, Microbial Enzymes and Conversions, A. H. Rose (Ed.), pp. 55–65 (1980).

*Primary Examiner*—Lionel M. Shapiro
*Assistant Examiner*—Jayme A. Huleatt
*Attorney, Agent, or Firm*—Fidelman, Wolffe & Waldron

[57] ABSTRACT

A storage stable liquid enzyme concentrate of Subtilisin Carlsberg containing 0.5–6.5 Anson Units of proteinase per gram of concentrate and method for preparing same. Solid form proteinase is extracted with 70–100 parts by volume propylene glycol, 30–0 parts by volume of water, then adjusted as necessary to 60–85% by wt. of the glycol. Stabilizing agents in the concentrate are 0.1–1 mol/kg. of one or more $C_1$–$C_3$ carboxylate, formate being preferred, and a calcium ion content of 0.04–0.5% by wt., pH range is 5–8.

7 Claims, No Drawings

LIQUID PROTEINASE CONCENTRATE AND METHOD FOR PREPARATION

The present invention relates to aqueous enzyme concentrates adapted for incorporation into liquid detergent formulations.

BACKGROUND OF THIS INVENTION

Incorporation of enzymes, particularly of proteinase into liquid detergent formulations has long been an objective of workers in the detergent arts. A particular difficulty that faced the art has been the rapid decrease of enzyme activity during storage of the liquid detergent product. To a substantial extent, the difficulty has been resolved by the art through inclusion of enzyme stabilizing ingredients such as lower alcohols, calcium ions, and organic acids. (See for example the teachings in U.S. Pat. Nos. 4,111,855 and 4,318,818.)

Successful stabilization of preteinase detergent formulations imposed upon the producers of the enzyme a requirement to supply enzyme in a form suited to use in the liquid formulations. Desirably, the enzyme supplier should provide a liquid enzyme concentrate adapted to the detergent formulation; indeed, the text of 4,318,818 appears to indicate that the stabilization system described therein is as applicable to liquid enzyme concentrates as to liquid detergent formulations.

However, the enzyme supplier must be concerned with storage stability of the enzyme concentrate as such, since significant delays can be encountered between preparation of the liquid enzyme concentrate by the enzyme supplier and delivery thereof to the detergent formulator. Both enzyme supplier and detergent formulator would be pleased if the liquid enzyme concentrate exhibited high enough stability to allow also for reasonable delay between delivery of the concentrate and dilution thereof into the detergent formulation without the need for cold storage.

Attention to stabilization of the enzyme concentrate is particularly important in the instance of Subtilisin Carlsberg, one industrial form of which is Alcalase ®.

BRIEF DESCRIPTION OF THE INVENTION

The present invention comprises a liquid enzyme concentrate of Subtilisin Carlsberg containing from 0.5–6.5 Anson Units per gram of concentrate in a solution of propylene glycol-1,2 and water; whereby the propylene glycol-1,2 constitutes 60–85% by wt. of the liquid enzyme concentrate and the water constitutes 10–35% by weight of the liquid enzyme concentrate. Preferred is 65–85% propylene glycol; most preferred is 65–80%, water being then 10–30% by wt., and 15–30% respectively.

In addition, Calcium$^{++}$ is present as from 0.04–0.5% w/w in the concentrate; preferably 0.04–0.3% by wt., most preferably 0.06–0.15% by wt.

Also present is a $C_1$–$C_3$ carboxylate ion in amounts of the formate, or acetate, or propionate from 0.1–1.0 mol/kg. The sodium, potassium or within the herein specified limits for Ca$^{++}$ the calcium salt of the carboxylate may be employed. Mixed carboxylates may be employed to a cumulative total of up to 1.0 mol/kg of concentrate. Preferred carboxylate content is 0.2–0.8 mol/kg, most preferred is 0.3–0.7 mol/kg.

The pH of the concentrate is in the range pH 5–8, and preferably pH 6–7.

DETAILED DISCUSSIONS OF THE INVENTION

As has been indicated, the Subtilisin Carlsberg of this invention is intended for dilution into liquid detergent formulations, forming from about 0.25%–2% of the final formulation, more usually from 0.5%–1%. The detergent formulation per se forms no part of this invention. Normally, the proteinase concentate of this invention will be supplied to soapers, who will incorporate the concentrate into their own preferred liquid detergent formulation as the proteinase component thereof.

It may be noted that the liquid proteinase concentrate of this invention may be employed with the detergent formulation materials as well as the general proportions described in U.S. Pat. No. 4,318,818, albeit that some adjustment in calcium ion and/or propylene glycol and/or caboxylate content may be required in the final detergent product if the objective is to employ some exact teaching of that patent, i.e., after dilution of the proteinase concentrate to the enzyme content contemplated for employment in a preferred mode liquid detergent formulation.

Although considerable attention has been paid to proteinase containing liquid detergents and the need for stabilizing the enzyme therein, relatively little attention has been paid to the need for stabilization of the liquid enzyme concentrates supplied to the soapers. One of the proteases most commonly employed in detergents, namely Subtilisin Carlsberg for which an exemplary trade name is Alcalase ® loses activity rapidly in aqueous solution concentrate form.

In addition, relatively little attention has been paid to how to prepare stable liquid form proteinase concentrates. That is not to say, however, that this invention occupies a vacant space in the art. Prior workers in the art have recognized the rapid activity loss exhibited by proteinase in aqueous solutions and that the activity loss be decreased substantially by presence of polyhydric alcohols, including propylene glycol, vide for example, U.S. Pat. No. 3,717,550 and Belgium Pat. No. 773,893 teachings. However, none of the prior art suggest the present composition, nor the ease with which the liquid proteinase concentrates of this invention can be prepared from the solid form enzyme concentrate products that result from state of the art fermentation and enzyme recovery techniques. This solid form proteinase concentrate product may contain a substantial amount of water, e.g., up to around 50% w/w.

To prepare the liquid proteinase concentrate of this invention, the solid form enzyme concentrate in activity quantities sufficient to generate the desired final activity of 0.5–6.5 Anson Units per gram of liquid concentrate, preferably 2–4 Anson Units per gram of liquid concentrate, more preferably 2–3 Anson Units per gram of liquid concentrate, is extracted with a 70–100/30–0 by volume mixture of propylene glycol and water. The extractant may be 100% propylene glycol. The resulting slurry is filtered or centrifuged to remove undissolved solids. The filtrate/supernatant may be the finished concentrate if the propylene glycol-water mixture had been doped appropriately with carboxylate salt and calcium ion beforehand, and the propylene glycol-water mixture employed causes the extract to be within the by weight proportions thereof described above for the liquid proteinase concentrate.

The pH of the liquid proteinase concentrate will ordinarily be in the desired pH 5–8 range, but pH adjustment as necessary, before and/or after inclusion of the enzyme into the propylene glycol-water mixture is contemplated. Addition of the $C_1$–$C_3$ carboxylate and of calcium ions to the propylene glycol-water mixture before or after inclusion of the enzyme therein is also contemplated.

Essentially, all of the proteinase is taken up in solution in the liquid, along with some non-enzymatic materials. Propylene glycol/water mixtures with a propylene glycol content of more than 70 parts of glycol to less than 30 parts of water (parts by volume) seems to be the superior extractant vis a vis the other alcohols suggested to the art, and vis a vis lower propylene glycol content mixtures.

In total, the liquid enzyme concentrate contains the below listed ingredients in the below given preferred proportions.

(1) Enzymatic activity corresponding to 2–3 Anson Units/g solution;

(2) Some non-enzymatic material from the solid form proteinase concentrate in an amount of around 0.005–0.05 g/g solution;

(3) A solvent which is a mixture of propylene glycol 1,2 and water in an amount of 60–85% by wt. and 10–35% by wt., respectively, in regard to the liquid enzyme concentrate;

(4) Additives according to the below indicated table:

| Ionic Additive | Exemplary Counter Ion | Concentration of Ionic Additive |
|---|---|---|
| $Ca^{++}$ | $Cl^-$, $NO^-_3$ | 0.04–0.5% w/w |
| $HCOO^-$ | $Na^+$, $K^+$, $Ca^{++}$ | |
| $CH_3COO^-$ | $Na^+$, $K^+$, $Ca^{++}$ | 0.1–1.0 mol/kg |
| $CH_3CH_2COO^-$ | $Na^+$, $K^+$, $Ca^{++}$ | |

Only one of the three carboxylate additives need be added, although more than one may be present. If more than one of the three carboxylate additives are added, the maximum sum of their concentrations is about 1.0 mol/kg. Since the $Ca^{++}$ concentration for stabilization is only about 0.01–0.13 mol/kg, the molar proportions of calcium ion to carboxylate ion is usually insufficient to allow calcium carboxylate to satisfy requirements for both the calcium and the carboxylate ions.

For further understanding of the present invention the following specific Examples are presented.

EXAMPLE 1

In all runs in this Example numerically identified hereinafter by a first digit of 7, the enzyme starting material was ALCALASE concentrate produced in accordance with the teachings appearing in Belgium Pat. No. 889,336, which concentrate, however, was not subjected to the final drying operation. Three parts of this protease starting material (for the sake of brevity in the following referred to as S) were suspended in ten parts of propylene glycol. The suspension was stored at ambient temperature for two days and then filtered. Subsequently, $CaCl_2$ and either sodium acetate or propionic acid, or no carboxylate were added in such amounts as to generate the concentrations indicated in Table 1A below, and the pH value was adjusted to 6.0 or 6.7, vide Table 1A, with 80% acetic acid or 12% NaOH, as the case may be. Finally, the liquid was germ filtered.

In all runs the first two digits of which are 10, one part of S was suspended in two parts of propylene glycol. The subsequent procedure was as indicated above for the runs in the 7-series, except that sodium formate (instead of sodium acetate or propionic acid) or no carboxylate was added, and pH was adjusted to 6.2, vide Table 1A.

The enzyme stability test results for the final liquids resulting from the runs in the 7- and 10-series are provided in Table 1B below, and the appearance-stability of the final liquid concentrates resulting from the 7- and 10-series are provided in Table 1C.

TABLE 1A

| Sample | Water %, w/w | Fatty acid residue** | Calcium as % Ca, w/w | pH | Activity AU/g |
|---|---|---|---|---|---|
| 701 | 14.0 | — | 0.005 | 6.0 | 1.86 |
| 1001 | 16.5 | — | 0.03 | 6.2 | 2.84 |
| 1004 | ~16 | — | 0.04 | 6.2 | 2.87 |
| 704 | 13.4 | — | 0.09 | 6.7 | 1.84 |
| 1007 | ~16 | — | 0.13 | 6.2 | 2.81 |
| 710 | 13.4 | — | 0.18 | 6.7 | 1.97 |
| 707 | 13.3 | — | 0.19 | 6.0 | 1.98 |
| 702 | 14.8 | 0.50 A | 0.03 | 6.0 | 1.81 |
| 703 | 14.1 | 0.50 P | 0.02 | 6.0 | 1.74 |
| 1002 | ~16 | 0.44 F | 0.03 | 6.2 | 2.73 |
| 705 | 14.4 | 0.50 A | 0.06 | 6.7 | 1.95 |
| 706 | 14.9 | 0.50 P | 0.05 | 6.7 | 1.83 |
| 1005 | 16.0 | 0.44 F | 0.07 | 6.2 | 2.85 |
| 1008 | ~16 | 0.44 F | 0.15 | 6.2 | 2.81 |
| 708 | 13.8 | 0.50 A | 0.21 | 6.0 | 1.84 |
| 709 | 13.5 | 0.50 P | 0.21 | 6.0 | 1.81 |
| 711 | 14.5 | 0.50 A | 0.22 | 6.7 | 1.86 |
| 712 | 17.7 | 0.50 P | 0.25 | 6.7 | 1.70 |
| 1003 | ~16 | 0.88 F | 0.04 | 6.2 | 2.70 |
| 1006 | ~16 | 0.88 F | 0.07 | 6.2 | 2.79 |
| 1009 | 15.4 | 0.88 F | 0.16 | 6.2 | 2.70 |

**mol/kg, A = acetate, F = formate, P = propionate; calculated from amount added.

TABLE 1B

| | Storage at 37° C.; % activity remaining after (weeks) | | | | | | |
|---|---|---|---|---|---|---|---|
| Sample | 1 | 2 | 4 | 6 | 8 | 16 | 26 or 28(*) |
| 701 | — | 90 | 81 | 69 | 67 | 52 | 39* |
| 1001 | 89 | 83 | 73 | — | 64 | 52 | 41 |
| 1004 | 100 | 97 | 96 | — | 78 | 69 | 60 |
| 704 | — | 90 | 77 | 72 | 67 | 56 | 40* |
| 1007 | 100 | 96 | 98 | — | 93 | 83 | 72 |
| 710 | — | 98 | 93 | 98 | 92 | 77 | (93*) |
| 707 | — | 95 | 96 | 100 | 96 | 89 | 77* |
| 702 | — | 90 | 95 | 88 | 90 | 78 | 64* |
| 703 | — | 100 | 86 | 97 | 85 | 66 | 54* |
| 1002 | 95 | 84 | 81 | — | 70 | 54 | 45 |
| 705 | — | 93 | 93 | 89 | 86 | 79 | 65* |
| 706 | — | 93 | 93 | 92 | 90 | 71 | 56* |
| 1005 | 96 | 87 | 95 | — | 95 | 88 | 76 |
| 1008 | 100 | 98 | 97 | — | 97 | 91 | 88 |
| 708 | — | 99 | 92 | 100 | 81 | 87 | 79* |
| 709 | — | 100 | 100 | 91 | 97 | 84 | (95*) |
| 711 | — | 81 | 90 | 97 | 100 | 76 | 77* |
| 712 | — | 100 | 95 | 99 | 99 | 78 | 72* |
| 1003 | 93 | 85 | 78 | — | 61 | 50 | 40 |
| 1006 | 96 | 100 | 93 | — | 91 | 83 | 77 |
| 1009 | 100 | 95 | 98 | — | 95 | 87 | 81 |

TABLE 1C

| Sample | Appearance after 16 weeks at 37° C. |
|---|---|
| 701 | cloudy; precipitate and white particles |
| 1001 | cloudy; precipitate and white particles |
| 1004 | clear; slight precipitate |
| 704 | cloudy; precipitate and white particles |
| 1007 | clear; slight precipitate |
| 710 | cloudy |
| 707 | cloudy; slight precipitate |
| 702 | clear; slight precipitate |
| 703 | clear; slight precipitate |

TABLE 1C-continued

| Sample | Appearance after 16 weeks at 37° C. |
|---|---|
| 1002 | cloudy; loose precipitate |
| 705 | OK, i.e. clear, no precipitate |
| 706 | OK, i.e. clear, no precipitate |
| 1005 | OK, i.e. clear, no precipitate |
| 1008 | clear; slight precipitate |
| 708 | clear; slight precipitate |
| 709 | clear; slight precipitate |
| 711 | OK, i.e. clear, no precipitate |
| 712 | OK, i.e. clear, no precipitate |
| 1003 | cloudy; loose precipitate |
| 1006 | clear; slight precipitate |
| 1009 | clear; slight precipitate |

EXAMPLE 2

In all runs 1 part of S was suspended in 2 parts of propylene glycol. After storage for one week at ambient temperature the liquid was filtered, and the filtrate was divided in three parts (221, 223, and 222).

To the first part (221) a mixture of water and propylene glycol was added in order to adjust the percentage of water and the activity of the protease to the value indicated in Table 2. Subsequently the pH was adjusted to the value indicated in Table 2 (around 6.4) and finally the liquid was germfiltered. For the sake of brevity this entire treatment described above in this paragraph will be referred to as treatment T.

To the second part (223) $CaCl_2$ was added in an amount as to generate the calcium concentration indicated in Table 2. Subsequently this calcium enriched liquid was treated according to treatment T.

To the third part (222) $CaCl_2$ and sodium formate were added in an amount as to generate the calcium and formate concentrations indicated in Table 2. Subsequently this calcium and formate enriched liquid was treated according to treatment T.

Finally run 27 was carried out as in run 222, but with a slightly higher concentration of calcium.

The test results are tabulated below in Table 2.

TABLE 2

| Sample | | 221 | 223 | 222 | 27 |
|---|---|---|---|---|---|
| Water, % | | 19.0 | 19.1 | 18.8 | 18.8 |
| Formate, mol/kg | | — | — | 0.48 | 0.52 |
| Calcium, as % Ca | | 0.010 | 0.059 | 0.068 | 0.10 |
| pH | | 6.45 | 6.32 | 6.42 | 6.4 |
| Activity, AU/g | | 2.81 | 2.93 | 2.78 | 2.85 |
| Storage at 37° C. | 1 week | 89 | 96 | 97 | 99 |
| | 2 weeks | 87 | 95 | 97 | 98 |
| % activity remaining after | 3 weeks | 79 | 94 | 95 | 97 |
| | 4 weeks | 76 | 91 | 94 | 95 |
| | 6 weeks | 67 | 85 | 92 | 93 |
| | 8 weeks | 64 | 82 | 90 | 94 |
| | 10 weeks | 61 | 80 | 89 | 93 |
| Appearance after 4 weeks | | slightly cloudy; loose, light precipitate | cloudy; (light) brown precipitate | clear; thin light precipitate | OK i.e. clear; no precipitate |

Examples 1 and 2 demonstrate that the stability of the liquid proteinase concentrate is excellent when the parameters thereof are kept inside the herein described limits.

For commercial practice of this invention the results desired after extended storage times (simulated by storage for some weeks at 37° C.) are clarity, absence of precipitate and a residual activity exceeding 80%, preferably exceeding 90%. The results of Example 2 are illustrative of what can be obtained by practice of this invention. The superiority of Samples 222 and 27 over control Samples 221 and 223 is unmistakable. Sample 27 self evidently illustrates a best mode for practice of the invention. However, the test results for Sample 222 are poor only by comparison with those of Sample 27. Moreover, the 37° C. test is an accelerated test. It is sometimes estimated that storage at 37° C. for two weeks corresponds to storage at 25° C. (a more realistic temperature for storage) for six months.

We claim:
1. A liquid enzyme concentrate comprising:
   the proteinase from Subtilisin Carlsberg in concentration of from 0.5–6.5 Anson Units per gram of concentrate;
   propylene glycol in an amount of 60–85% and water in an amount of 10–35% by wt.;
   calcium ion in concentration of about 0.04–0.5% by wt.;
   a water soluble carboxylate in concentration of 0.1–1.0 mol/kg selected from the group consisting of formate, acetate, propionate and mixtures thereof, the pH being in the range of 5–8.
2. The concentrate of claim 1 wherein the caboxylate is formate.
3. The concentrate of claim 2 wherein the formate concentration is in the range of 0.3–0.7 mol/kg.
4. The concentrate of claim 1 wherein the pH of the concentrate is in the range of pH 6–7.
5. The concentrate of claim 1 wherein the enzyme concentration is in the range of 2–4 Anson Units per gram.
6. The concentrate of claim 1 wherein the calcium ion content is in the range of 0.06–0.15% by wt.
7. The concentrate of claim 1 wherein the propylene glycol content is 65–80% by wt. and the water content is 15–30% by wt.

* * * * *